United States Patent
Sunami et al.

(10) Patent No.: US 9,958,429 B2
(45) Date of Patent: May 1, 2018

(54) SUBSTRATE FOR CONTROLLING MOVEMENT DIRECTION OF ANIMAL CELLS, AND CELL IDENTIFICATION METHOD AND CELL SEPARATION METHOD USING THE SAME

(71) Applicant: JAPAN SCIENCE AND TECHNOLOGY AGENCY, Kawaguchi-shi, Saitama (JP)

(72) Inventors: Hiroshi Sunami, Ginowan (JP); Ikuko Yokota, Sapporo (JP)

(73) Assignee: JAPAN SCIENCE AND TECHNOLOGY AGENCY, Kawaguchi-Shi (JP)

( * ) Notice: Subject to any disclaimer, the term of this patent is extended or adjusted under 35 U.S.C. 154(b) by 0 days. days.

(21) Appl. No.: 15/033,224

(22) PCT Filed: Nov. 6, 2014

(86) PCT No.: PCT/JP2014/079421
§ 371 (c)(1),
(2) Date: May 26, 2016

(87) PCT Pub. No.: WO2015/068759
PCT Pub. Date: May 14, 2015

(65) Prior Publication Data
US 2016/0274080 A1   Sep. 22, 2016

(30) Foreign Application Priority Data
Nov. 6, 2013  (JP) ................................. 2013-229898

(51) Int. Cl.
*G01N 33/00* (2006.01)
*G01N 33/483* (2006.01)
(Continued)

(52) U.S. Cl.
CPC ......... *G01N 33/4833* (2013.01); *C12M 47/04* (2013.01); *C12N 5/0068* (2013.01); *G01N 33/5005* (2013.01); *C12N 2535/00* (2013.01)

(58) Field of Classification Search
None
See application file for complete search history.

(56) References Cited

U.S. PATENT DOCUMENTS 5,427,663 A * 6/1995 Austin ................. B01J 19/0093
204/450
6,468,531 B1 * 10/2002 Matthew ............ C07K 16/4241
424/131.1
(Continued)

FOREIGN PATENT DOCUMENTS

FR  2 980 208 A1  3/2013
FR  2 980 209 A1  3/2013
(Continued)

OTHER PUBLICATIONS

European Patent Office, "Extended European Search Report," issued in EP Patent Application No. 14 861 042.1, which is a European counterpart of U.S. Appl. No. 15/033,224, dated Jun. 22, 2017, 5 pages.
(Continued)

*Primary Examiner* — Jill A Warden
*Assistant Examiner* — Brittany I Fisher

(57) ABSTRACT

The present invention provides a control substrate for controlling a movement direction of animal cells. The control substrate for controlling a movement direction of animal cells has a surface which includes a plurality of grooves, the grooves are formed from a bottom between opposing walls and the opposing walls forming the grooves wherein the walls include a plurality of columnar protrusions. Vertex parts of the columnar protrusion are formed to face between
(Continued)

vertex parts of two columnar protrusions formed in the opposing wall and such vertex parts face the same direction.

9 Claims, 13 Drawing Sheets

(51) Int. Cl.
*G01N 33/50* (2006.01)
*C12N 5/00* (2006.01)
*C12M 1/00* (2006.01)

(56) References Cited

U.S. PATENT DOCUMENTS

| | | | |
|---|---|---|---|
| 2005/0106756 A1* | 5/2005 | Blankenstein | B01L 3/502753 436/523 |
| 2005/0202733 A1* | 9/2005 | Yoshimura | B01L 3/502746 439/839 |
| 2011/0293558 A1* | 12/2011 | Suresh | B01L 3/502746 424/85.2 |
| 2012/0261356 A1* | 10/2012 | Tsutsui | B01L 3/502761 210/767 |
| 2013/0210068 A1* | 8/2013 | Yokoyama | C12Q 1/045 435/34 |
| 2013/0301105 A1* | 11/2013 | Kim | G02B 26/005 359/290 |
| 2014/0251666 A1* | 9/2014 | Arai | C23C 18/1216 174/257 |
| 2015/0004692 A1 | 1/2015 | LeBerre et al. | |
| 2015/0184122 A1 | 7/2015 | LeBerre et al. | |

FOREIGN PATENT DOCUMENTS

| | | |
|---|---|---|
| JP | 2009-022276 A | 2/2009 |
| JP | 2013-179912 A | 9/2013 |
| JP | 2013-208098 A | 10/2013 |
| WO | 2012/049784 A1 | 4/2012 |

OTHER PUBLICATIONS

Hiroshi Sunami et al., "Control of Cell Migration by Using Three-Dimensional Pattern," the 33rd Annual Meetings of the Molecular Biology Society and the 83rd Annual Meetings of the Biochemical Society of Japan (Nov. 19, 2010).

Hiroshi Sunami, "Development of New Cytotaxis Using a Three-Dimensional Pattern", strategic target "production of a next generation nano system by process integration", the Joint Symposium of Three Research Areas (Oct. 17, 2013).

Hiroshi Sunami et al., "Sanjigen Pattern o Riyo Shita Saibo Bunri", Regenerative Medicine, vol. 10, Suppl 2011, p. 271, 2P-124 (Feb. 1, 2011).

International Search Report received for PCT Application No. PCT/JP2014/079421 dated Feb. 10, 2015, 4 pages (2 pages of English Translation of International Search Report, 2 pages of International Search Report).

* cited by examiner

SUBSTRATE FOR CONTROLLING MOVEMENT DIRECTION OF ANIMAL CELLS, AND CELL IDENTIFICATION METHOD AND CELL SEPARATION METHOD USING THE SAME

CROSS REFERENCE TO RELATED APPLICATIONS

This patent application is a U.S. national stage application under 35 U.S.C. § 371 of International Patent Application No. PCT/JP2014/079421 filed on Nov. 6, 2014, which claims the benefit of foreign priority to Japanese Patent Application No. JP 2013-229898 filed on Nov. 6, 2013. The International Application was published in Japanese on May 14, 2015, as International Publication No. WO 2015/068759 A1 under PCT Article 21(2).

TECHNICAL FIELD

The present invention relates to a substrate for controlling a movement direction of animal cells, and a method of identifying cells and a method of separating cells using the substrate, which can identify or separate cells using a difference of moving capabilities between cells.

Priority is claimed on Japanese Patent Application No. 2013-229898, filed Nov. 6, 2013, the content of which is incorporated herein by reference.

BACKGROUND ART

Cells in movable environments such as blood, a lymphatic fluid or a liquid culture medium have characteristics in which they move (migrate) in response to a chemical stimulus which are caused by a chemical substance, a growth factor or the like. Cells also migrate in response to an electrical stimulus, a physical stimulus such as a contact stimulus, or other external factors in such environments. Research and development have been conducted on methods, a device, an instrument and a material used for the method, wherein a stimulus by which cell migration is promoted is selected and used to specifically identify and separate target cells from a heterogeneous cell group, with a focus on the moving capability of cells.

A plurality of research examples in which cell migration is controlled by cell chemotaxis in response to a chemical substance have been provided so far, and a cytologic diagnosis using chemotaxis has become practical as an application. As an exemplary method in which cells are separated and diagnosed using chemotaxis, there is a method using a Boyden chamber that is divided into upper and lower compartments separated by a porous filter. In this method, a chemical substance for attracting specific cells is provided in the compartment below the filter of the Boyden chamber, and various cells are seeded in the compartment above the filter. Therefore, it is possible to observe the movement of cells in a direction of the compartment below the filter and to collect the cells that moved.

However, in the method of separating cells using chemotaxis, there is a risk in which, since cells are stimulated with a chemical substance or a growth factor, properties of cells such as differentiation, proliferation, and functional expression of target cells are influenced, and the properties of cells before and after stimulation may be changed. That is, since chemotaxis tends to destabilize properties of the target cells, use of chemotaxis is disadvantageous in a cell therapy or diagnosis in which stimulated cells are administered into a living body.

On the other hand, by providing a so-called scaffold formed of a suitable material such as silicon for cells, a method is proposed in which a difference of migration capabilities between cells that move on the scaffold is used to identify or separate the cells. For example, methods (Non-Patent document 1 and Non-Patent document 2) are reported in which, a migration direction of cells is controlled when cells are seeded on a substrate on which a regular pattern having a regular triangular prismatic shape of a micro order is formed on a silicon substrate using a photoresist technology or on a substrate having a surface on which protrusions are formed.

When cell migration is induced using the scaffold as a stimulant, properties of cells are less likely to be changed before and after stimulation unlike in chemotaxis. Accordingly, research on structural characteristics and properties of the scaffold, and a migration capability and a direction control of cells is proceeding.

CONVENTIONAL ART DOCUMENTS

Non Patent Documents

Non-Patent document 1: "Control of Cell Migration Using a Three-Dimensional Pattern," the 33rd Annual Meetings of the Molecular Biology Society and the 83rd Annual Meetings of the Biochemical Society of Japan, Nov. 19, 2010.

Non-Patent document 2: "Development of New Cytotaxis Using a Three-Dimensional Pattern," strategic goal "production of a next generation nano system by process integration," the Joint Symposium of Three Research Areas, Oct. 17, 2013.

DISCLOSURE OF INVENTION

Problem to be Solved by the Invention

The present invention provides a new substrate and method in which a substrate having a distinctive micro pattern is provided as a scaffold to cells instead of chemotaxis using a chemical substance, a growth factor or an antibody, and a migration capability of cells is used to identify or separate the cells.

Means for Solving the Problem

The inventors focused that cells preferably migrate through protrusions of a scaffold, found that it is possible to control a migration direction of cells by continuously arranging protrusions in a predetermined direction, and completed the following inventions.

(1) A control substrate which controls a movement direction of animal cells, wherein a surface of the substrate includes a plurality of grooves, the grooves are formed from two opposing walls and a bottom provided between the two opposing walls, and the two opposing walls forming the grooves include continuous columnar protrusions, wherein the columnar protrusions i) have a shape wherein each columnar protrusion has at least one vertex part in a horizontal cross section; and ii) are provided at the positions such that columnar protrusions formed in a wall and columnar protrusions formed in the opposing wall are arranged alternately.

(2) The substrate according to item (1), wherein an interval between vertex parts of adjacent columnar protrusions in a single wall is 3 µm to 20 µm.
(3) The substrate according to item (1) or (2), wherein the wall has a height of 10 to 40 µm.
(4) The substrate according to any of items (1) to (3), wherein a distance between the opposing walls is 2 µm to 20 µm.
(5) The substrate according to any of items (1) to (4), wherein a direction of the protrusions is inclined to one direction with respect to a distance direction in which the distance toward the opposing wall is measured.
(6) The substrate according to item (5), wherein a direction of the protrusions faces a direction of 10 and 80 degrees with respect to a perpendicular direction toward the opposing wall.
(7) The substrate according to any of items (1) to (6) wherein the columnar protrusion has a horizontal cross-sectional shape that is a polygon with six or less sides.
(8) The substrate according to any of items (1) to (7), wherein the substrate is made of a material selected from the group consisting of silicon, glass, a plastic and a metal.
(9) A method of identifying cells of two or more different types based on a moving capability, the method including: adding a cell suspension including cells of two or more different types to one end of the groove of the substrate according to any of items (1) to (8); maintaining the substrate under conditions in which the cells survive; and identifying a type of the cells along a groove direction of the groove of the maintained substrate.
(10) A method of separating cells of two or more different types based on a moving capability, the method including: adding a cell suspension including cells of two or more different types to one end of the groove of the substrate according to any of items (1) to (8); maintaining the substrate under conditions in which the cells survive; and collecting cells on the maintained substrate.

Effects of Invention

According to the present invention, when a cell suspension is seeded on a substrate of the present invention, it is possible to identify or separate cells while maintaining original functions of the cells. In addition, when a separation process of cells and the number of moved cells on the substrate are monitored using a microscope or other devices, it is possible to evaluate an abundance of cells of each type in the cell suspension or biological tissue, and invasiveness of cancerous cells.

In addition, according to the present invention, since it is not necessary to use a chemical substance, a growth factor, and an antibody in order to move cells, it is possible to separate cells while maintaining properties of the cells, and to provide stable cells desirable for a cytologic diagnosis and a cell therapy.

BEST MODE FOR CARRYING OUT THE INVENTION

The present invention relates to a control substrate for controlling a movement direction of animal cells (hereinafter referred to as "cells"). In the control substrate for controlling a movement direction of animal cells, a surface of the substrate includes a plurality of grooves, the grooves are formed from a bottom between two opposing walls, and the two opposing walls forming the grooves include continuous columnar protrusions, wherein the columnar protrusions i) have a shape whose protrusion includes at least one vertex part in a horizontal cross section; and ii) are provided at the positions such that columnar protrusions which are formed in a wall and columnar protrusions which are formed in the opposing wall are arranged alternately.

Note that the term "movement of cells" in the present invention refers to a transfer of cells, that is, a migration of cells.

When cells suspended in a suitable solvent are seeded on the substrate of the present invention, cells having a high moving capability start their own migration, enter or fall into the grooves, and then migrate through the grooves in one direction along vertex parts of the continuous columnar protrusions of the wall. On the other hand, cells having a low moving capability barely move or slightly move from a portion at which they are seeded on a scaffold. As a result, the cells having a high moving capability and the cells having a low moving capability are positioned to be separated from each other on the substrate. The substrate of the present invention is a substrate for controlling a movement direction of the cell, that is, a migration direction of the cell, in this manner.

Figure 1:
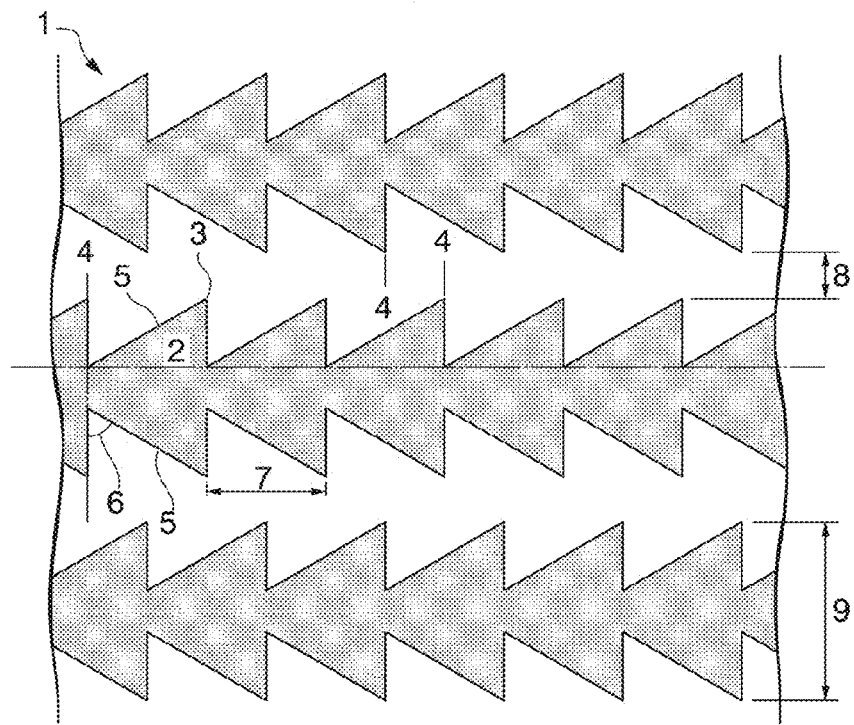
FIG. 1 is a view schematically showing a microstructure of a substrate according to an embodiment of the present invention.
Figure 2:
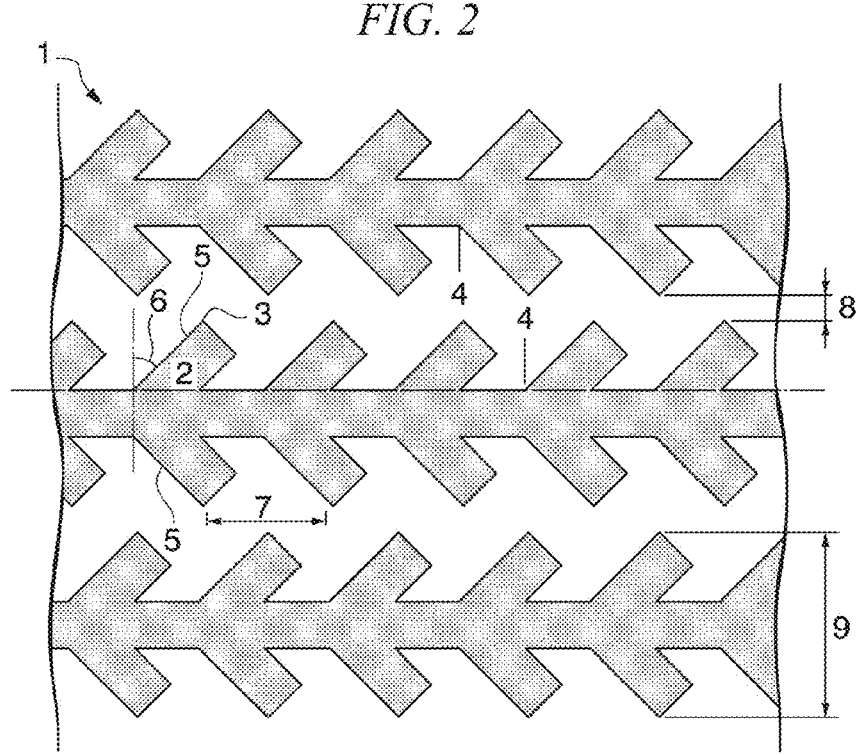
FIG. 2 is a view schematically showing a microstructure of a substrate according to another embodiment of the present invention.

FIGS. 1 and 2 show exemplary embodiments of walls and grooves in the substrate of the present invention. Hereinafter, a description will be provided with reference to the drawings.

Figure 3:
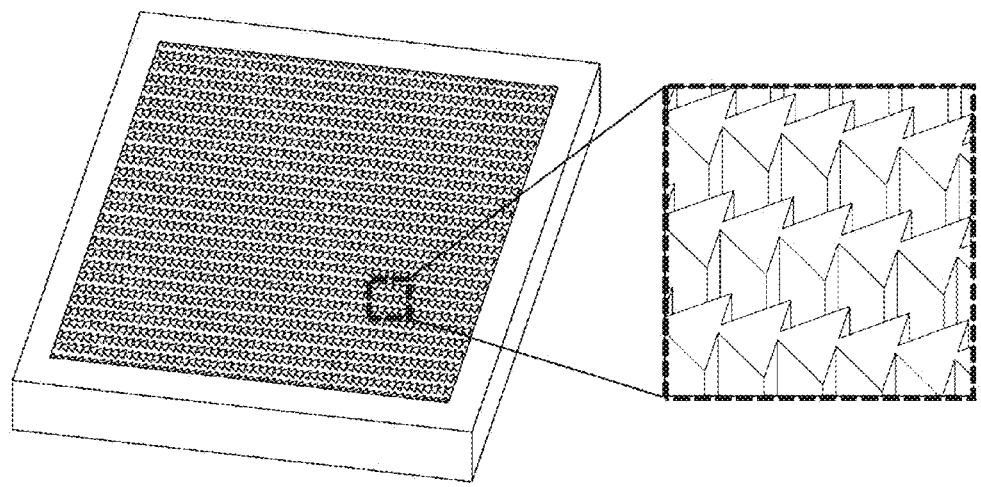
FIG. 3 is a perspective view of the substrate shown in FIG. 1.

In FIGS. 1 and 2, when the substrate is viewed directly from the top, shaded sections represent two or more opposing walls 1 and colorless portions (spaces) between the opposing walls represent the grooves. In addition, for convenience of illustration, a bottom positioned in an inner direction of a sheet surface is not shown. In addition, FIG. 3 is a perspective view of the substrate of the embodiment of FIG. 1.

In the wall 1 in the embodiment of the invention shown in FIG. 1, columnar protrusions 2 whose cross-sectional shapes when the wall 1 is cut in a horizontal direction are triangles are continuously provided at both sides of the wall 1. The columnar protrusion 2 of the wall 1 is formed to face an area between vertex parts 3 of two columnar protrusions of the opposing wall 1, and as a result, is provided such that the columnar protrusions 2 of the wall 1 and the columnar protrusions 2 formed in the opposing wall 1 are arranged alternately. The columnar protrusion 2 is a partial structure of the wall 1 that is integrally formed with the wall 1 so as to rise from the bottom (refer to the perspective view of FIG. 3).

The phrase "columnar protrusions formed in a wall and columnar protrusions formed in the opposing wall are arranged alternately" can also mean "columnar protrusions are formed such that, when a perpendicular line 4 with respect to two opposing walls 1 is drawn, vertex parts that are closest to the opposing wall 1 among the columnar protrusions 2 of the two walls 1 are not on one perpendicular line."

In addition, the phrase "each columnar protrusion has at least one vertex part in a horizontal cross section" can mean "a columnar protrusion has at least one corner part." A shape (a cross-sectional shape when the wall 1 is cut in a horizontal direction) of the columnar protrusion 2 of the wall 1 in the present invention is not particularly limited except that at least one vertex part on which cells are able to be caught during migration is provided. The vertex part of the present invention may have a corner at an angle of 90 degrees or less, preferably 60 degrees or less, and more preferably 30 degrees or less, when a shape (a cross-sectional shape when the wall is cut in the horizontal direction) of the columnar protrusion 2 is a polygon.

The columnar protrusion 2 in the present invention is continuously provided in a direction in which the wall 1 extends. A repetition pitch thereof can be represented as an interval 7 between the vertex parts 3 of the columnar protrusions. In the substrate of the present invention, the columnar protrusion 2 is preferably formed such that the interval between the vertex parts 3 of the columnar protrusions has a range of 3 µm to 20 µm, and preferably 10 µm to 15 µm.

The height of the columnar protrusion 2 may be the same as the height of the wall 1.

In addition, in the present invention, a direction of the protrusions is preferably inclined in one direction with respect to a distance direction of the opposing wall. In the embodiment shown in FIG. 1, any one side 5 (a hypotenuse of a triangle) of the columnar protrusion 2 of the opposing wall 1 is formed to face a right direction of the drawing at a gradient 6 with respect to a perpendicular line of the wall 1. The columnar protrusion 2 in the present invention is preferably formed such that the gradient 6 has a range of 10 to 80 degrees, and preferably 30 degrees to 75 degrees. A migration direction of cells is controlled in a direction facing the protrusion.

The height of the wall 1 (a depth of the groove) in the present invention is preferably regulated to 5 µm to 40 µm, and more preferably to 20 to 30 µm. When the height of the wall 1 (the depth of the groove) is less than 5 µm, a frequency at which cells migrating through the groove climb atop the wall 1 increases, and control efficiency of a migration direction tends to decrease. Also, even when the height of the wall 1 is greater than 40 µm, a control of the migration direction is not particularly difficult, and an upper limit thereof depends on a technology for manufacturing the substrate.

The opposing wall 1 in the present invention is preferably formed such that a distance therebetween becomes 2 µm to 20 µm, and preferably 5 µm to 15 µm. The distance herein refers to a distance 8 between a surface connecting vertex parts 3 of columnar protrusions of one wall 1 and a surface connecting vertex parts 3 of columnar protrusions of the other wall 1. When the distance is greater than the above range, the migration speed of cells tends to decrease.

A width 9 of the wall in the present invention is preferably regulated to 20 µm to 60 µm, and more preferably to 30 to 50 µm. When the width is greater than the upper limit, cells seeded on the substrate are less likely to move or fall in the groove, and much time may be consumed for an operation of identifying or separating cells.

Reference signs of FIG. 2 showing another embodiment of the substrate of the present invention correspond to reference signs of FIG. 1. The wall 1 of the embodiment of FIG. 2 includes a plurality of columnar protrusions 2 whose cross-sectional shapes when the wall 1 is cut in a horizontal direction are trapezoids at both sides of the wall. In the embodiment, the vertex part 3 (a corner that is closest to the opposing wall within the trapezoid) of the columnar protrusion of one wall 1 is formed to face an area between vertex parts 3 of two columnar protrusions of the other wall 2, and the vertex parts 3 of the wall 1 and the other wall 2 are positioned alternately. In addition, all protrusions of the columnar protrusions 2 of the opposing walls 1 are formed to face a right direction of the drawing.

Note that, while the columnar protrusion 2 whose shape (a cross-sectional shape when the wall is cut in a horizontal direction) is a polygon is shown in the embodiments of FIGS. 1 and 2, the columnar protrusion 2 in the present invention may have a cross-sectional shape formed in a curve, for example, a semielliptical shape or a wave shape. In addition, the vertex part of the columnar protrusion 2 may have an angle of 90 degrees or less, preferably 60 degrees or less, and more preferably 30 degrees or less, and the vertex part may have a hairpin shape having a corresponding degree of curvature. In addition, an interval between the above-described vertex parts, and a distance, a height and a width of the wall may be uniform in a single substrate and a single wall, or may be different within the above range. For example, in a single substrate, walls having a different interval between vertex parts, the different height and/or width may be provided. In addition, an interval between vertex parts or a width of vertex parts of a single wall may be partially different.

A material of the substrate of the present invention is not particularly limited as long as the material can form a microstructure of a micron order. Exemplary appropriate materials may include silicon, glass, a plastic, and a metal. The silicon or glass can be used to produce the substrate of the present invention using a photolithographic technique for forming a microstructure.

Particularly, the material of a preferred substrate is a silicon wafer on which a microstructure of a micron order can be formed using the photolithographic technique.

The photolithographic technique for forming a microstructure on a silicon wafer is a technique commonly known in the field of manufacturing a semiconductor element or a print substrate including processes in which a photomask is produced, and a pattern is formed in a wafer form, and other processes. Many methods such as a positive photoresist and a negative photoresist have been developed. In order to manufacture the substrate of the present invention, any photolithographic technique using a silicon wafer or the like as a target can be used.

Also, when the substrate of the present invention is manufactured from a silicon wafer using the photolithographic technique, in order to ensure a height of the wall (a depth of the groove) of the substrate of the present invention, deep etching such as a bosch process is preferably performed.

In the substrate of the present invention, cells suspended in a suitable liquid solvent, and preferably, in a liquid culture medium, are seeded on the substrate, and the cells move in the groove. Therefore, for example, when the substrate manufactured using a silicon wafer as a material by the photolithographic technique has a hydrophobic surface, it is preferable that hydrophilic treatment be performed on a surface for usage. The substrate whose surface has hydrophilicity in this manner is a preferable embodiment of the present invention.

As a method of hydrophilizing the surface of the substrate, a known method may be used depending on a material to be used. For example, an $O_2$ plasma method and a surfactant treatment method can be used for the substrate manufactured from a silicon wafer.

The substrate which is based on a silicon wafer and manufactured by the photolithographic technique can also be used as a template for transferring a pattern to another material. For example, a suitable plastic, a thermosetting resin or thermoplastic resin are liquefied or dissolved in a solvent, are poured in the substrate and solidified, and thus it is possible to produce a substrate of the present invention using a plastic or the like as a material. Alternatively, a pattern may be transferred to a plastic material by pressing the substrate formed of a silicon wafer onto the plastic material. In addition, when a metal is used as a material, a pattern of the present invention may be directly formed on the metal by micro laser processing or the like so that the substrate of the present invention can be manufactured.

As still another embodiment, the present invention provides a method of identifying cells of two or more different types based on a moving capability. The method includes a process of adding a cell suspension including the cells of two or more different types to one end of a groove of the aforementioned substrate, a process of maintaining the substrate under conditions in which the cells are able to survive, and a process of identifying types of the cells in a groove direction of the maintaining substrate.

In addition, as yet another embodiment, the present invention provides a method of separating cells of two or more different types based on a moving capability. The method includes a process of adding a cell suspension including the cells of two or more different types to one end of a groove of the aforementioned substrate, a process of maintaining the substrate under conditions in which the cells are able to survive, and a process of collecting the cells on the maintaining substrate.

In the above methods, the one end of the groove of the substrate refers to an end in a direction opposite to a direction in which the vertex part of the columnar protrusion of the wall described above faces (is inclined toward), and refers to an end positioned on the left side of the drawing when a method using the substrates shown in FIGS. 1 and 2 is exemplified.

Figure 15:
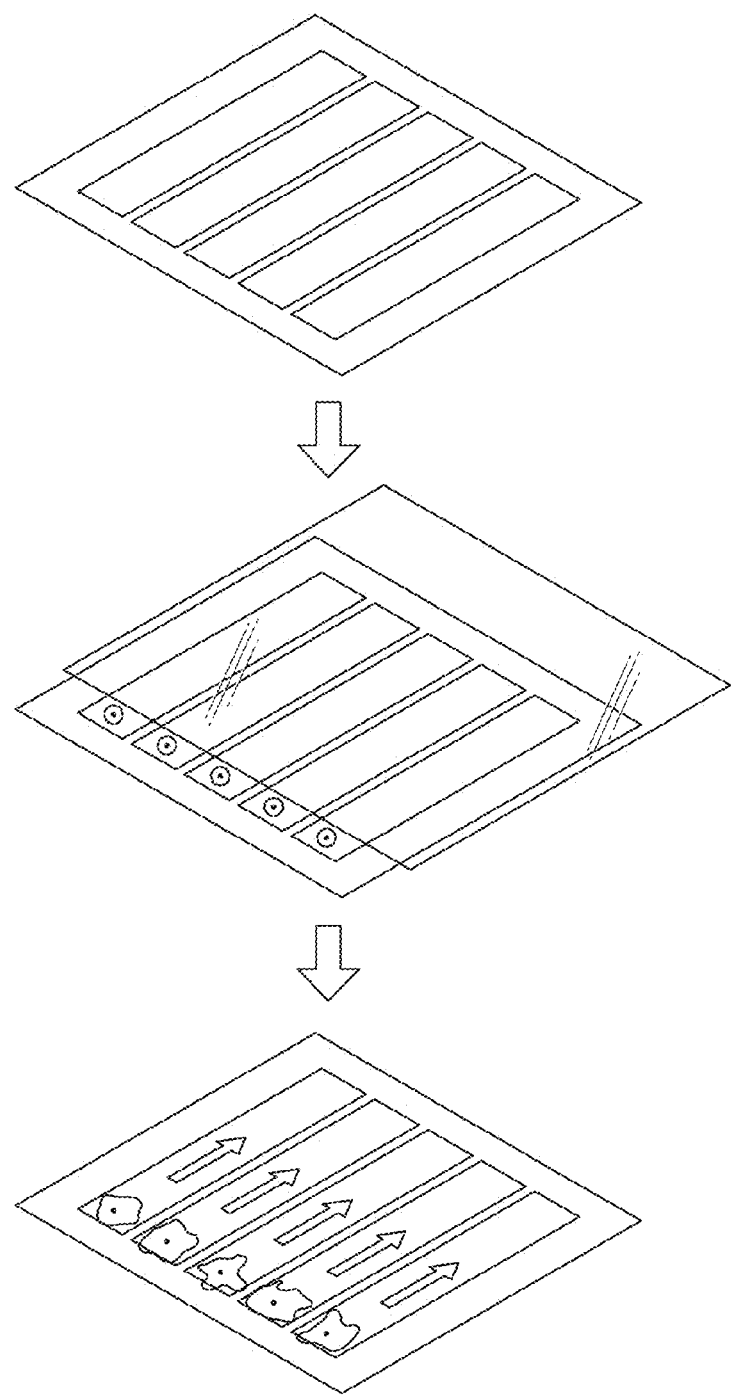
FIG. 15 is a view schematically showing a structure and a usage method of a substrate according to another embodiment of the present invention.

In addition, as yet another embodiment, a covering member such as a cover glass is placed on the substrate so as to cover at least a part of the above-described substrate (the wall), and the cell suspension including the cells of at least one type is added to the substrate that is not covered. Then, the covering member is removed and cell migration can be started (FIG. 15).

A typical example of the method of the present invention is performed such that the substrate is immersed in a suitable liquid, preferably, in a liquid culture medium or a buffer solution that is appropriate for survival of separation target cells, a suspension including the target cells is seeded at one end in a direction in which the groove of the substrate extends and is left for several hours to several days under conditions in which the cells are able to survive, for example, under an aerobic environment at a temperature of about 37° C. In particular, the substrate of the present invention is put into a container such as a petri dish, and a DMEM medium or other liquid culture mediums suitable for culturing animal cells are added to the petri dish to an extent that an upper surface of the substrate is slightly immersed. Then, the cell suspension is dropped at one end in the direction in which the groove of the substrate extends, and may be left for 10 hours to 24 hours under cell culture conditions.

As the culture medium, the buffer solution and the conditions under which it is left, those that are known to those skilled in the art as appropriate for cells may be selected depending on cells to be identified or separated. In addition, the cells can be identified by external observation of the cells using a microscope, observation using optical characteristics, cell labeling using a fluorescent reagent having specificity to cells or a chemical substance such as an antibody, and by applying other methods that are generally used to identify cells. In addition, in cells that are localized at different portions on the substrate due to a different migration capability, one or both thereof can be collected by a suitable method, and therefore separated.

When the substrate of the present invention is used, cells having a high moving capability and cells having a low moving capability can be identified or separated without using a special chemical substance. For example, cancerous cells are known to have a higher moving capability than normal cells. Therefore, a cell suspension prepared from a specimen extracted or collected by, for example, a biopsy, is seeded on the substrate of the present invention, properties of cells are examined by focusing on moving cells, and thus it is expected to be possible to perform diagnosis of cancer.

In addition, it is generally known that iPS cells have a low moving capability, and cells that are induced to be differentiated into specific cells show a high moving capability. Therefore, when the substrate of the present invention is used, it is possible to identify or separate target cells that are differentiation-induced from iPS cells and the remaining undifferentiated iPS cells. In particular, according to the method of the present invention, a chemical substance for controlling migration directionality is not necessarily required to separate cells, and a possibility of properties of cells being changed before and after separation is extremely low or almost zero. Such a separation technology is advantageous in that it is possible to provide stable cells desirable for a cytologic diagnosis and a cell therapy.

Furthermore, when the substrate of the present invention is applied to a medical instrument such as a vascular stent, a catheter, and an artificial joint, cells having a low motility remain on a surface of the medical instrument implanted into a living body, whereas cells having a high motility can be detached from the substrate. The surface of the medical instrument is covered with desired cells, and it is expected to be possible to increase biocompatibility.

The present invention will be described in further detail with reference to the following examples.

EXAMPLES

Example 1

(1) Manufacture of a Substrate Having a Three-Dimensional Pattern

Figure 4:
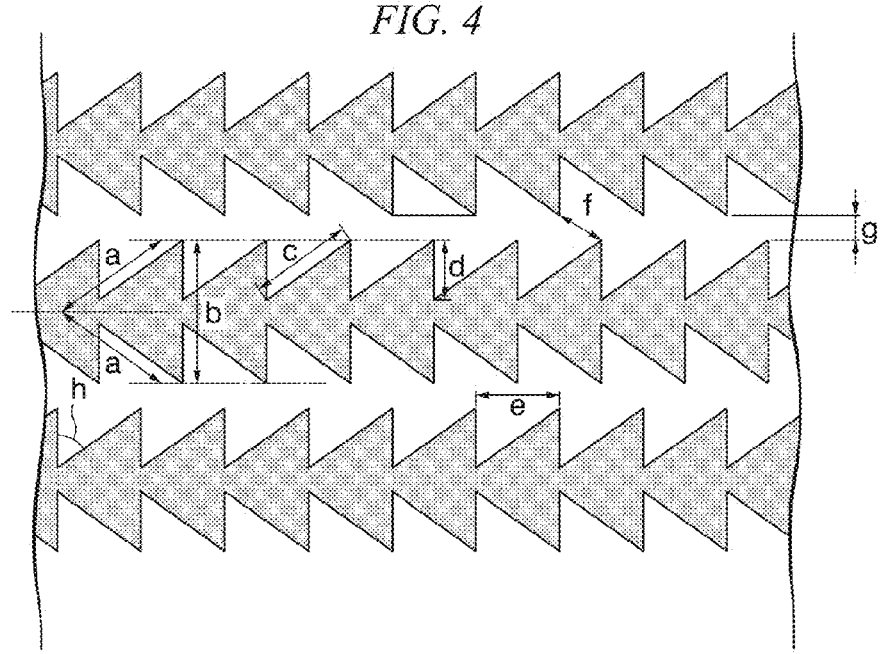
FIG. 4 shows a basic pattern of a photomask used for manufacturing a substrate of the present invention.

With respect to areas of quartz photomasks (commercially available from MITANI MICRONICS Co., Ltd.) having 25 areas (squares of 1 mm), photomasks that have a basic structure shown in FIG. 4 and have 15 types of patterns 1 to 15 in which portion dimensions and angles indicated by a to h are different were prepared.

On a silicon substrate (10 mm×10 mm) having a thermally oxidized film of 900 nm, hexamethyldisilazane (MMDS, commercially available from TOKYO OHKA KOGYO Co., Ltd.) and a resist composition (OFPR-5000LB, commercially available from TOKYO OHKA KOGYO Co., Ltd.) were spin-coated (1000 rpm for 5 seconds to 4000 rpm for 45 seconds). After a prebake was performed (110° C. for 2 minutes), the previously prepared quartz photomasks and the silicon substrate coated with a resist film were inserted into an exposure device (MA-20, commercially available from MIKASA Co., Ltd.) and exposed for 1.5 seconds.

The exposed silicon substrate was immersed and developed in a developing solution (NMD-3, commercially available from TOKYO OHKA KOGYO Co., Ltd.). A pattern of the resist film was checked using an optical microscope, and formation of the pattern of the resist film on the silicon substrate was confirmed. After a postbake was performed (130° C., 20 minutes), $SiO_2$ of a portion which was not covered with the resist film on the silicon substrate was removed using a reactive ion etching device RIE-10-NRV (commercially available from Samco Co., Ltd.). Removal of $SiO_2$ was confirmed using FE-SEM JSM-6700FT (commercially available from JEOL Japan Electronics Co., Ltd.). Then, RIE-10-NRV (commercially available from Samco Co., Ltd.) was used to perform $O_2$ cleaning (50 sccm, 3 Pa, 3 minutes). Then, ultrasonic washing with acetone was performed for 30 seconds, and the resist film was completely removed.

An ICP dry etching device (MUC-21, commercially available from Sumitomo Precision Products Co., Ltd.) was used to deeply etch silicon ($SF_6$, 50 sccm, $C_4H_8$, 50 sccm, 500 W, 22 minutes, 4.7 Pa). $SiO_2$ used as the mask was removed with HF. When a cross section of the silicon substrate was observed using FE-SEM JSM-6700FT (commercially available from JEOL Japan Electronics Co., Ltd.), it was confirmed that a groove having a depth of 23 μM was formed.

Figure 5:
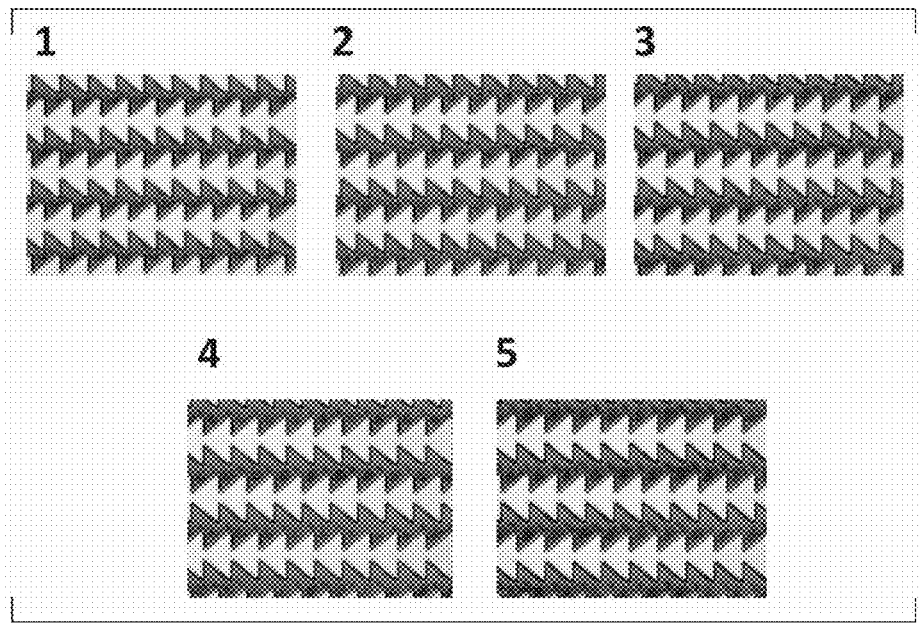
FIG. 5 shows microscope pictures of patterns of substrates 1 to 5.
Figure 6:
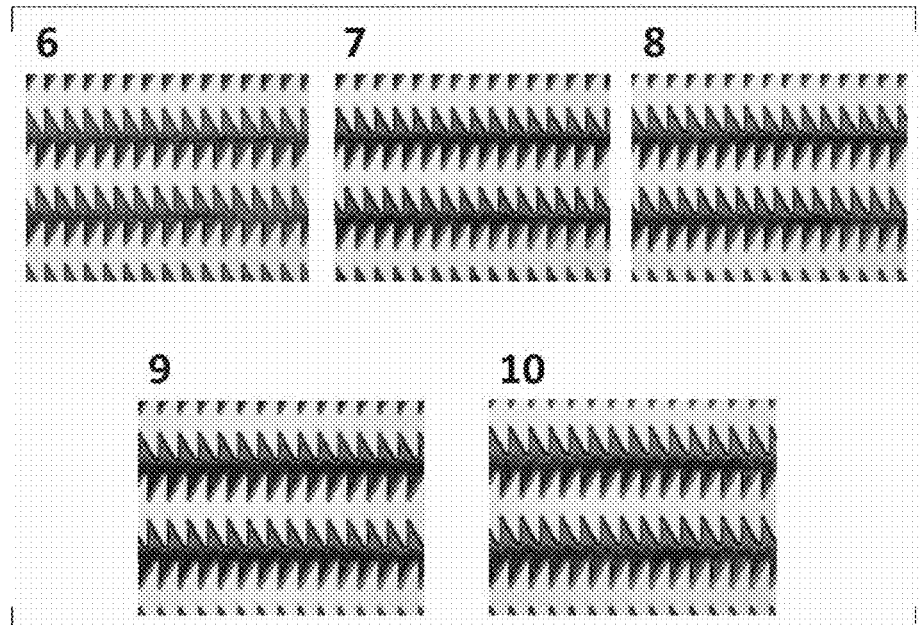
FIG. 6 shows microscope pictures of patterns of substrates 6 to 10.
Figure 7:
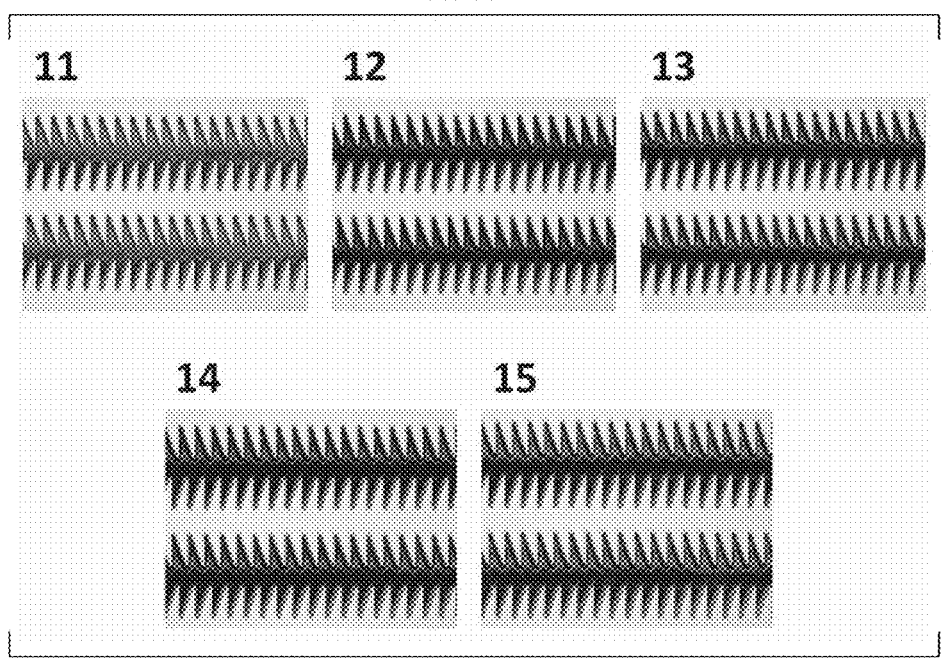
FIG. 7 shows microscope pictures of patterns of substrates 11 to 15.

A color laser 3D microscope (VK-9700, commercially available from KEYENCE) was used to observe a shape of the obtained three-dimensional pattern. In this case, while Real Peak Detection (RPD) was performed using a 50× objective lens (commercially available from Nikon Corp), observation was performed in a high definition mode. Based on such observation, in all of the patterns 1 to 15 prepared with the photomasks, it was confirmed that the substrates 1 to 15 of the present invention having patterns were manufactured in which a plurality of walls having continuous columnar protrusions of a triangular prism shape which were deviated at a predetermined range and opposing walls which were arranged in lines. The patterns of the substrates 1 to 15 are collectively shown in FIGS. 5 to 7.

Form analysis of pattern shape images of the substrates 1 to 15 was performed. For each substrate, lengths of portions indicated by a to h of FIG. 4 were measured at six different parts, and an average value and a standard deviation of the portions were calculated. The results are shown in Table 1.

TABLE 1

|  | Substrate 1 | Substrate 2 | Substrate 3 | Substrate 4 | Substrate 5 |
| --- | --- | --- | --- | --- | --- |
| a [μm] | 18.38068197 | 18.82886441 | 18.93502196 | 19.50432829 | 19.28011908 |
| ±SD | 0.541199238 | 0.4111633 | 0.232731797 | 0.356424246 | 0.59755981 |
| b [μm] | 23.77583333 | 24.099 | 23.86816667 | 24.74533333 | 24.83766667 |
| ±SD | 0.208518025 | 0.463509655 | 0.591942368 | 0.647651038 | 0.335463659 |
| c [μm] | 14.01143046 | 13.63512615 | 14.22609622 | 14.44218717 | 14.50724837 |
| ±SD | 0.224808119 | 0.367905288 | 0.140712987 | 0.347332982 | 0.198900739 |
| d [μm] | 8.217666667 | 7.666846798 | 7.620680131 | 8.079166667 | 8.217666667 |
| ±SD | 0.647651038 | 0.232448305 | 0.343984602 | 0.113084776 | 0.28608437 |
| e [μm] | 13.85369333 | 13.75955024 | 13.85372950 | 13.8056431 | 13.80383333 |
| ±SD | 0.175143627 | 0.224363891 | 0.171676411 | 0.274944848 | 0.208518025 |
| f [μm] | 8.613233801 | 7.546332352 | 8.179008806 | 9.921584109 | 10.23058028 |
| ±SD | 0.104765411 | 0.273894222 | 0.274201996 | 0.359634979 | 0.315785123 |
| g [μm] | 3.554833333 | 4.385833333 | 5.586166667 | 6.417166667 | 6.925 |
| ±SD | 0.113084776 | 0.208518025 | 0.113084776 | 0.113084776 | 0.247756332 |
| h [Degree] | 50.91771126 | 51.64632392 | 51.64096861 | 51.1323066 | 51.10807141 |
| ±SD | 0.981875181 | 0.755906002 | 0.637151462 | 0.347825408 | 0.437457935 |

TABLE 2

|  | Substrate 6 | Substrate 7 | Substrate 8 | Substrate 9 | Substrate 10 |
|---|---|---|---|---|---|
| a [μm] | 20.47198058 | 20.3523897 | 19.87022325 | 19.62100115 | 19.53864142 |
| ±SD | 0.398716117 | 0.512802887 | 0.405100914 | 0.452085212 | 0.263325318 |
| b [μm] | 35.87291517 | 35.22516667 | 35.8715 | 35.45673862 | 35.13356032 |
| ±SD | 0.456177264 | 0.53759889 | 0.339254329 | 0.552671847 | 0.208718682 |
| c [μm] | 13.77791341 | 13.70945266 | 13.94416817 | 14.28747823 | 14.45913549 |
| ±SD | 0.239501072 | 0.170304438 | 0.18918077 | 0.148021434 | 0.154631623 |
| d [μm] | 11.22075069 | 11.63625069 | 11.91314613 | 12.00547946 | 11.95716667 |
| ±SD | 0.154263491 | 0.244780171 | 0.247812096 | 0.225177086 | 0.272344206 |
| e [μm] | 9.325666667 | 9.325666667 | 9.187166667 | 9.233333333 | 9.2795 |
| ±SD | 0.143042185 | 0.226169553 | 0.113084776 | 0.143042185 | 0.151719148 |
| f [μm] | 7.378563653 | 7.709029818 | 9.077548067 | 9.2080299 | 10.61148724 |
| ±SD | 0.102832436 | 0.166298867 | 0.146377312 | 0.208119746 | 0.103543156 |
| g [μm] | 5.9555 | 6.601833333 | 7.663666667 | 7.8945 | 9.233333333 |
| ±SD | 0.151719148 | 0.113084776 | 0.143042185 | 0.231754827 | 0.143042185 |
| h [Degree] | 29.74073456 | 29.22892664 | 29.79154955 | 29.20031416 | 29.67343686 |
| ±SD | 0.279036768 | 0.67205718 | 0.370845795 | 0.487217637 | 0.168980778 |

TABLE 3

|  | Substrate 11 | Substrate 12 | Substrate 13 | Substrate 14 | Substrate 15 |
|---|---|---|---|---|---|
| a [μm] | 21.63333848 | 22.47993633 | 21.95056396 | 21.97151101 | 22.2976354 |
| ±SD | 0.198327502 | 0.354542447 | 0.418504945 | 0.587198607 | 0.19645964 |
| b [μm] | 41.827 | 42.84446142 | 42.84444228 | 42.79828325 | 43.30683185 |
| ±SD | 0.247756332 | 0.484671744 | 0.517268318 | 0.340702842 | 0.33724657 |
| c [μm] | 14.88274641 | 15.23023988 | 15.2609656 | 15.24906736 | 15.36764491 |
| ±SD | 0.363317371 | 0.258072343 | 0.217397845 | 0.261809037 | 0.198780871 |
| d [μm] | 13.76327973 | 14.2211431 | 13.85738519 | 13.94783495 | 14.21933333 |
| ±SD | 0.333636244 | 0.141702769 | 0.175143589 | 0.286119844 | 0.28608437 |
| e [μm] | 7.479 | 7.620915075 | 7.482415075 | 7.525166667 | 7.485708498 |
| ±SD | 0.175190182 | 0.229445212 | 0.175389784 | 0.208518025 | 0.181629102 |
| f [μm] | 7.607662699 | 8.758722717 | 9.230723817 | 9.826609464 | 10.85450885 |
| ±SD | 0.282810393 | 0.128575442 | 0.129986803 | 0.179229246 | 1.521894805 |
| g [μm] | 6.371 | 7.986833333 | 8.4485 | 9.371833333 | 10.06433333 |
| ±SD | 0.175190182 | 0.208518025 | 0.151719148 | 0.272344206 | 0.143042185 |
| h [Degree] | 19.30717129 | 18.82186922 | 19.16423668 | 19.55456358 | 19.7705559 |
| ±SD | 0.711888174 | 0.655746905 | 0.498179777 | 0.450746167 | 0.414179367 |

(2) Hydrophilizing, Sterilization and Surface-Degassing of Three-Dimensional Pattern The substrates 1 to 15 manufactured in (1) were subjected to $O_2$ cleaning (50 sccm, 3 Pa, 8 minutes) using RIE-10NRV (commercially available from Samco Co., Ltd.), and thus hydrophilicity (an affinity to water) was added to the substrates. The substrates 1 to 15 were sterilized at 120° C. for 20 minutes, immersed at a bottom of a 35 mm cell culture dish to which a DMEM medium including 10% FBS, 1% penicillin and streptomycin (hereinafter referred to as a "DMEM medium") was added, and degassed at −0.09 Mpa for one minute while lightly shaking. When a reflected image was observed using an optical microscope, it was confirmed that bubbles were completely removed. The hydrophilized substrates 1 to 15 were used for the following experiment.

Example 2

(1) PKH26 Staining of NIH3T3 Cells

The substrates manufactured in Example 1(2) were immersed at a bottom of the 35 mm cell culture dish to which the DMEM medium was added and degassed at −0.09 Mpa for one minute while lightly shaking, and after the culture medium was replaced, immersed in the culture medium and left for 12 hours without change. The NIH3T3 cells were seeded at $1 \times 10^4$ cells/cm$^2$ in the dish containing the substrate having a three-dimensional pattern, cultured for 2 hours, and then immersed in PKH26 (500-fold dilution, commercially available from Sigma-Aldrich Co. LLC) for 4 minutes at room temperature. A reaction of PKH26 was stopped by FBS, and then washing was performed with the culture medium. A time from when the NIH3T3 cells were stained with PKH26 until the washing operation was completed was about 0.25 hours. Such procedures were modified and used with reference to a staining protocol of PKH26.

Figure 8A:
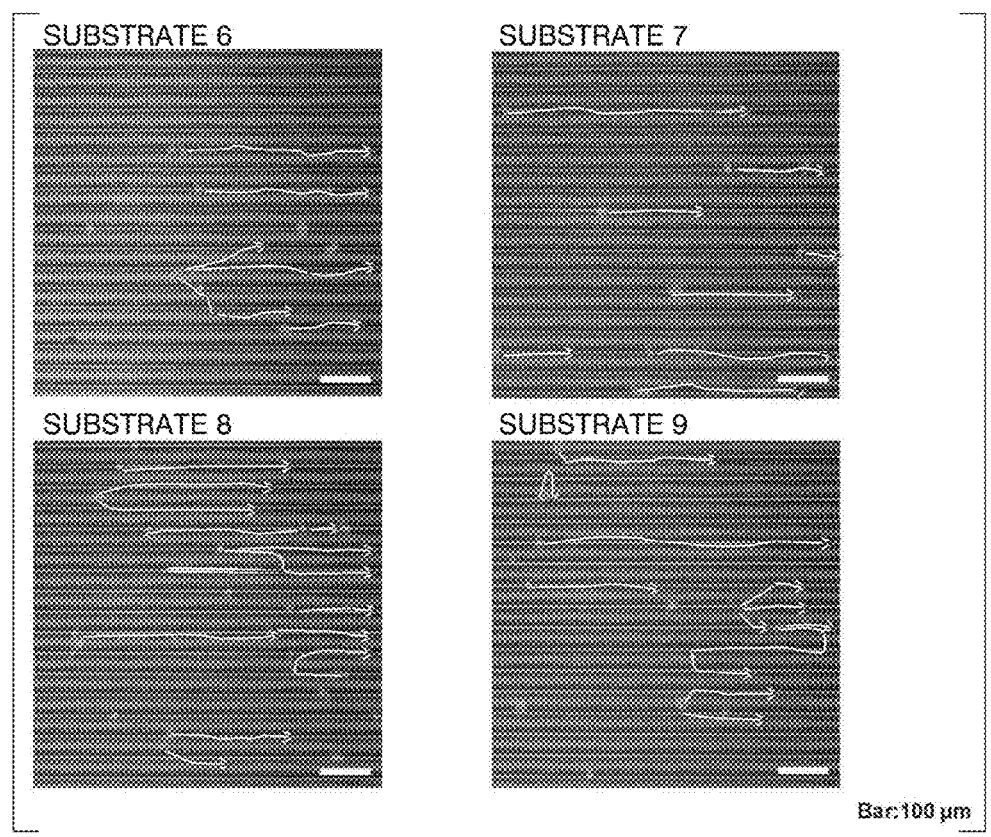
FIG. 8A shows microscope pictures of movement trajectories (lines in the drawing) of NIH3T3 cells that are seeded on a substrate of the present invention.
Figure 8B:
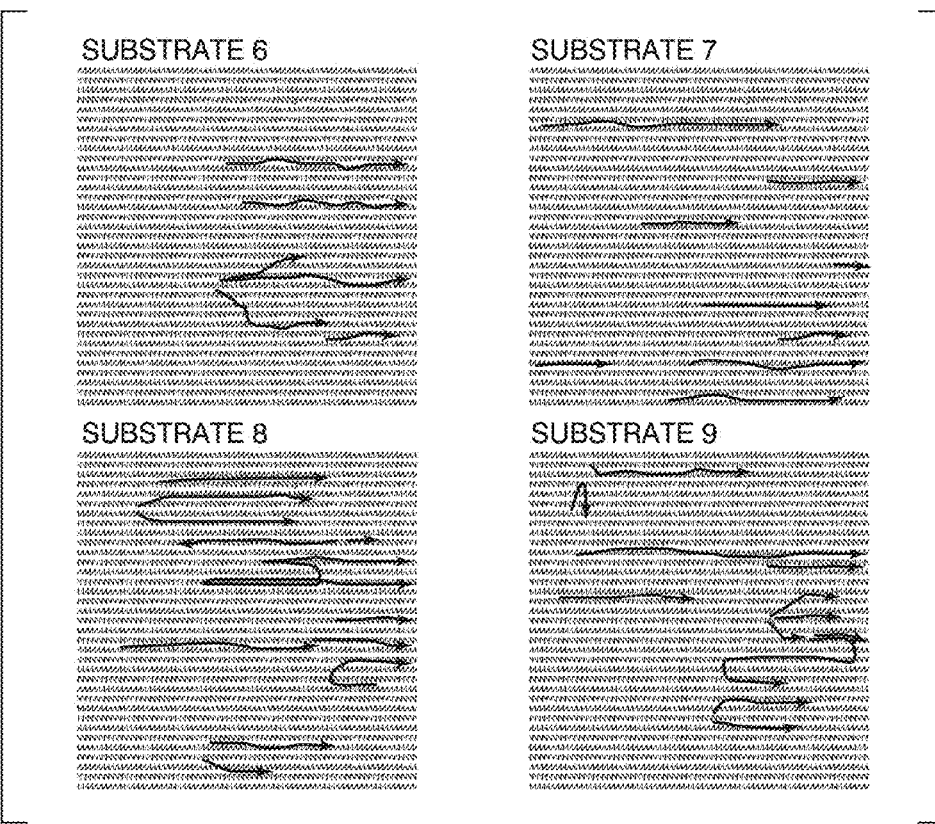
FIG. 8B shows schematic views of the microscope pictures (FIG. 8A) of movement trajectories (lines in the drawing) of NIH3T3 cells that are seeded on the substrate of the present invention.

The substrates to which the NIH3T3 cells stained with PKH26 were adhered were transferred into a Glass Base Dish (Glass 12φ, commercially available from IWAKI) filled with the culture medium, and placed to be inverted with respect to a portion of a glass window at the bottom of the dish. In this case, four vertex parts of each of the substrates were caught on a frame of the glass window, a gap between a cell seeding surface and a glass became sufficiently available, and the culture medium was diffused on the cell culture surface. In this state, the cells were additionally cultured in the DMEM medium for 1.75 hours. Then, a fluorescence microscope (ObserverZ1, commercially available from Zeiss) to which StageTop (registered trademark) Incubation INU-ZILCS (commercially available from TOKAI HIT Corp) was attached was used to perform time lapse observation at 30-minute intervals for 72 hours. A 10× objective lens was used for the observation. A reflected image of a three-dimensional pattern at designated fixed points (871 μm×690 μm) and a fluorescent image of the cells labeled with PKH26 were captured by a CCD camera. A moving image was generated from images obtained at the fixed points, and a cell migration direction was confirmed from the moving image. As a result, in all of the substrates 1 to 15, it was confirmed that the NIH3T3 cells migrated only in a direction (a right direction in FIG. 4) in which the vertex parts of the columnar protrusions protrude. Photographs obtained by capturing the exemplary substrates 6 to 9 and performing digital processing of trajectories of cells are shown in FIG. 8A. In addition, FIG. 8B is a schematic illustration of FIG. 8A in order for substrate patterns and cell trajectories in FIG. 8A to be clearly visible.

(2) PKH26 and PKH67 Staining of Living Cells of Two Types

The substrates manufactured in Example 1(2) were immersed at a bottom of the 35 mm cell culture dish to which the DMEM medium was added and degassed at −0.09 Mpa for one minute while lightly shaking, and after the culture medium was replaced, immersed in the culture medium and left for 12 hours without change. HeLa cells and HaCaT cells were separately seeded at $1 \times 10^4$ cells/cm$^2$ in the dishes containing the substrate, cultured in the DMEM medium for 9.75 hours, and then immersed in PKH67 (250-fold dilution) for 4 minutes at room temperature. A reaction of PKH67 was stopped by FBS, and then washing was performed with the culture medium. A time from when cells were stained with PHK67 until the washing operation was completed was about 0.25 hours. Such procedures were modified and used with reference to a staining protocol of PHK67.

Next, NIH3T3 cells dissociated by trypsin were washed with the DMEM medium, and immersed in PKH26 (250-fold dilution) for 4 minutes at room temperature. A reaction of PKH26 was stopped by FBS, and then washing was performed with the culture medium. NIH3T3 cells stained with PKH-26 were seeded at $1 \times 10^4$ cells/cm$^2$ in the substrates to which HeLa cells or HaCaT cells stained with PKH67 were adhered. A time from when cells were stained with PKH26 until the washing operation was completed was about 0.25 hours.

The cells were cultured in the DMEM medium for 5.75 hours. Then, the substrates were transferred into a Glass Base Dish (Glass 12φ) filled with the culture medium, and placed to be inverted with respect to a portion of a glass window at the bottom of the dish. In this case, four vertex parts of each of the substrates were caught on a frame of the glass window, a gap between a cell seeding surface and a glass became sufficiently available, and the culture medium was diffused on the cell culture surface. In this state, time lapse observation was performed similarly to (1).

Figure 9A:
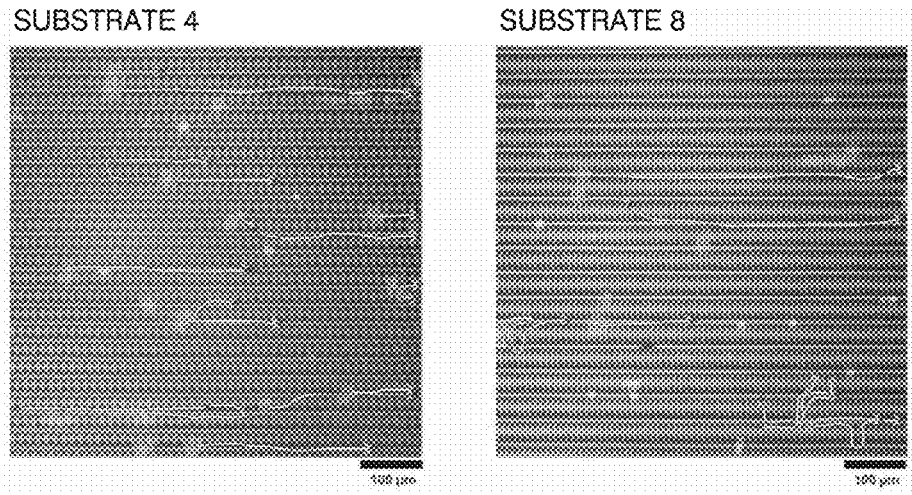
FIG. 9A shows microscope pictures of movement trajectories of NIH3T3 cells and HaCaT cells that are seeded on the substrate of the present invention. In the pictures, the green color indicates HaCaT cells, and a red color and lines indicate the NIH3T3 cells and trajectories thereof.
Figure 9B:
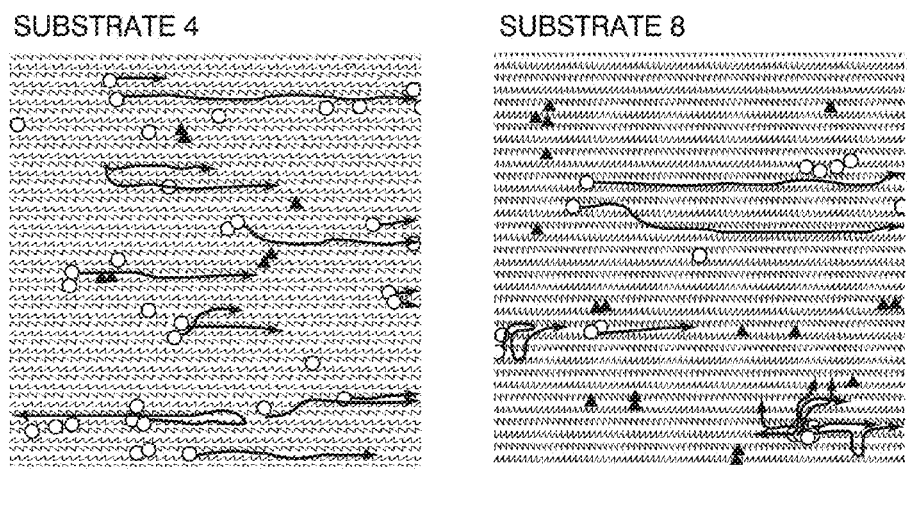
FIG. 9B shows schematic views of the microscope pictures (FIG. 9A) of movement trajectories of NIH3T3 cells and HaCaT cells that are seeded on the substrate of the present invention.

HaCaT cells (indicated by green and black Δ) and NIH3T3 cells (indicated by red and ○) were seeded on the same substrate and continuously observed at fixed points for 72 hours, and pictures obtained by performing digital processing of trajectories of cells are shown in FIG. 9A. In addition, FIG. 9B is a schematic illustration of FIG. 9A in order for substrate patterns and cell trajectories in FIG. 9A to be clearly visible. As can been seen from the pictures, the HaCaT cells (Δ) hardly moved, but all of the NIH3T3 cells (○) migrated in a right direction. The result shows that it is possible to identify or separate HaCat cells and NIH3T3 cells using the substrate of the present invention.

(3) Immobilization, DAPI Staining and Observation of Sample

The substrates 5 to 9 containing cells after the time lapse observation of (1) and (2) was performed were immersed in a 4% paraformaldehyde phosphate buffer solution, and the cells were immobilized. Cell nucleuses were stained using DAPI (commercially available from Dojindo Laboratories, 2000-fold dilution) for 20 minutes at room temperature, and sealed on a cover glass using EUKITT (registered trademark, commercially available from O. Kindler). Adherent cells were observed using a confocal laser scanning microscope (FV-1000D, commercially available from Olympus Corp). In this case, as an objective lens, a 40× lens or a 100× lens was used. Forms of a fluorescent image and a pattern of the cell nucleuses as well as a reflected image of cells were observed in a three-dimensional manner. Fluorescent staining of cells was performed with phalloidin-Alexa546. Three-dimensional observation was performed to a depth of 30 μm from a vicinity of a surface of the substrate at intervals of 0.5 μm. Images when cells on the substrate were viewed directly from the top and whose cross sectional views on the substrate were generated. All foci of images of the cells and the substrate viewed directly from the top were summed. The results are shown in FIG. 10.

Figure 10:
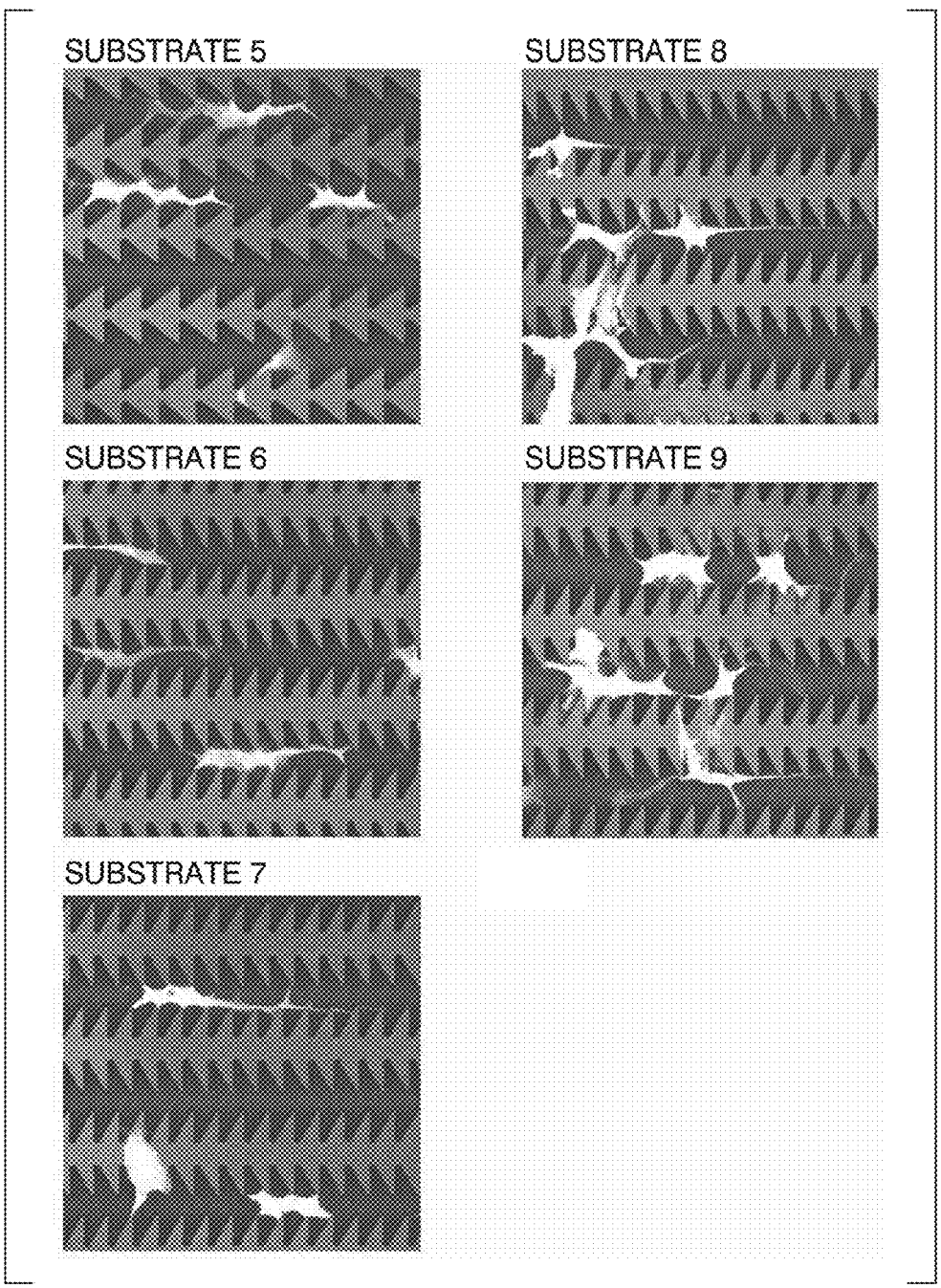
FIG. 10 shows microscope pictures of NIH3T3 cells that move in grooves of a substrate of the present invention.

In FIG. 10, it was confirmed that the cells seeded on the substrate of the present invention migrated through the groove along the vertex part of the columnar protrusion.

(4) Confirmation of Migration Directionality of Cells of One Type

In order to exactly determine whether cells move in one direction, a migration direction of NIH3T3 cells on the substrate of Example 2(1) was observed.

Figure 11:
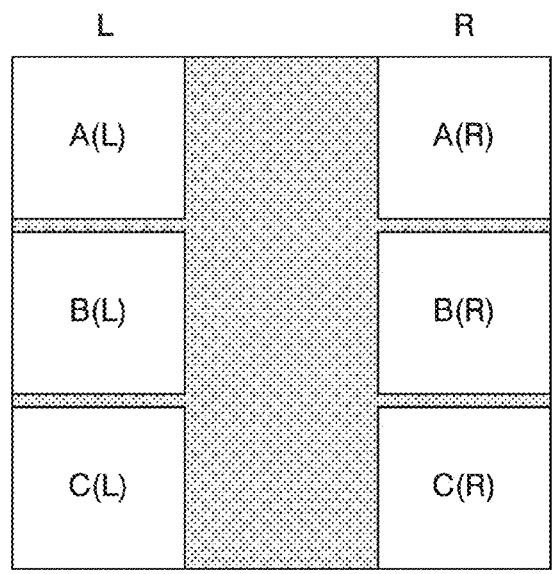
FIG. 11 is a view schematically showing areas of a substrate of the present invention.

An observation area of each of the substrates (1 mm×1 mm) was divided into a left (L) area and a right (R) area, and further divided into three areas, areas A to C (FIG. 11).

Pictures of the substrates were captured, the number of cells in each of the areas was counted, and an abundance ratio of the numbers of cells in the area R and the area L with respect to the total number of cells in the area R and the area L of the areas A to C was obtained. Further, an average value and a standard deviation of the abundance ratios of the area R and the area L of the areas A to C were calculated.

Figure 12:
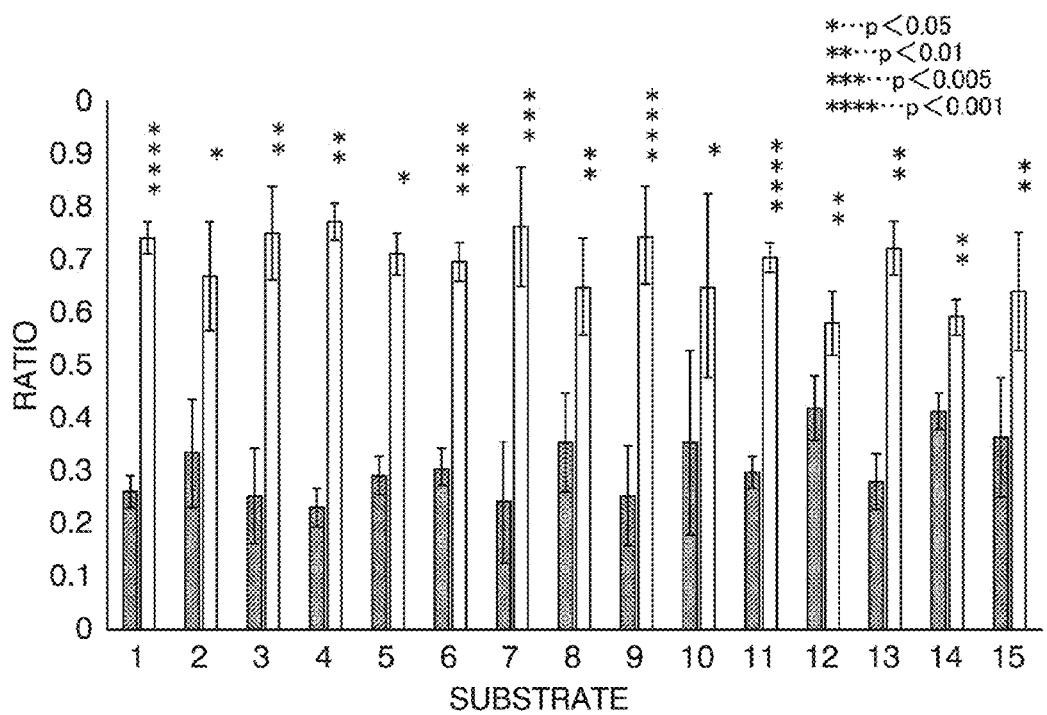
FIG. 12 is a graph showing the number of NIH3T3 cells that are observed in an area R and an area L of a scaffold in the substrates 1 to 15.

The result is shown in FIG. 12. In the drawing, a left (a shaded) bar graph of each group represents a ratio of the number of cells in the area L with respect to the total number of cells. A right (a white) bar graph of each group represents the ratio of the number of cells in the area R with respect to the total number of cells. An error bar represents the standard deviation.

Figure 13:
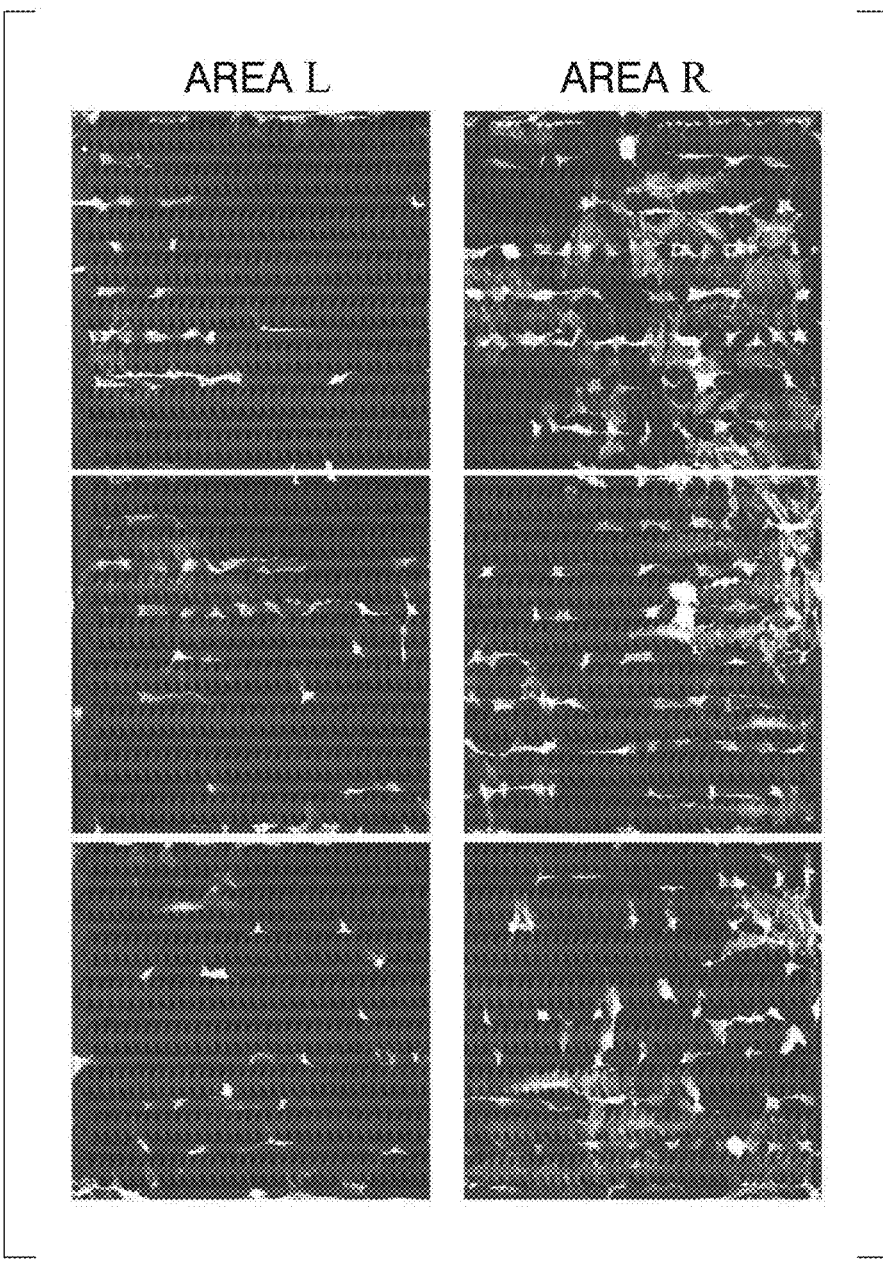
FIG. 13 shows microscope pictures of NIH3T3 cells of an area R and an area L of the substrate 9.

In addition, a picture obtained by capturing the substrate 9 is shown in FIG. 13.

In the substrate 9, it was confirmed that cells were greatly unevenly distributed in the area R. In addition, in the substrates 1 to 15, it was also confirmed that cells were significantly unevenly distributed in the area R.

(5) Confirmation of Migration Directionality of Cells of Two Types

Figure 14:
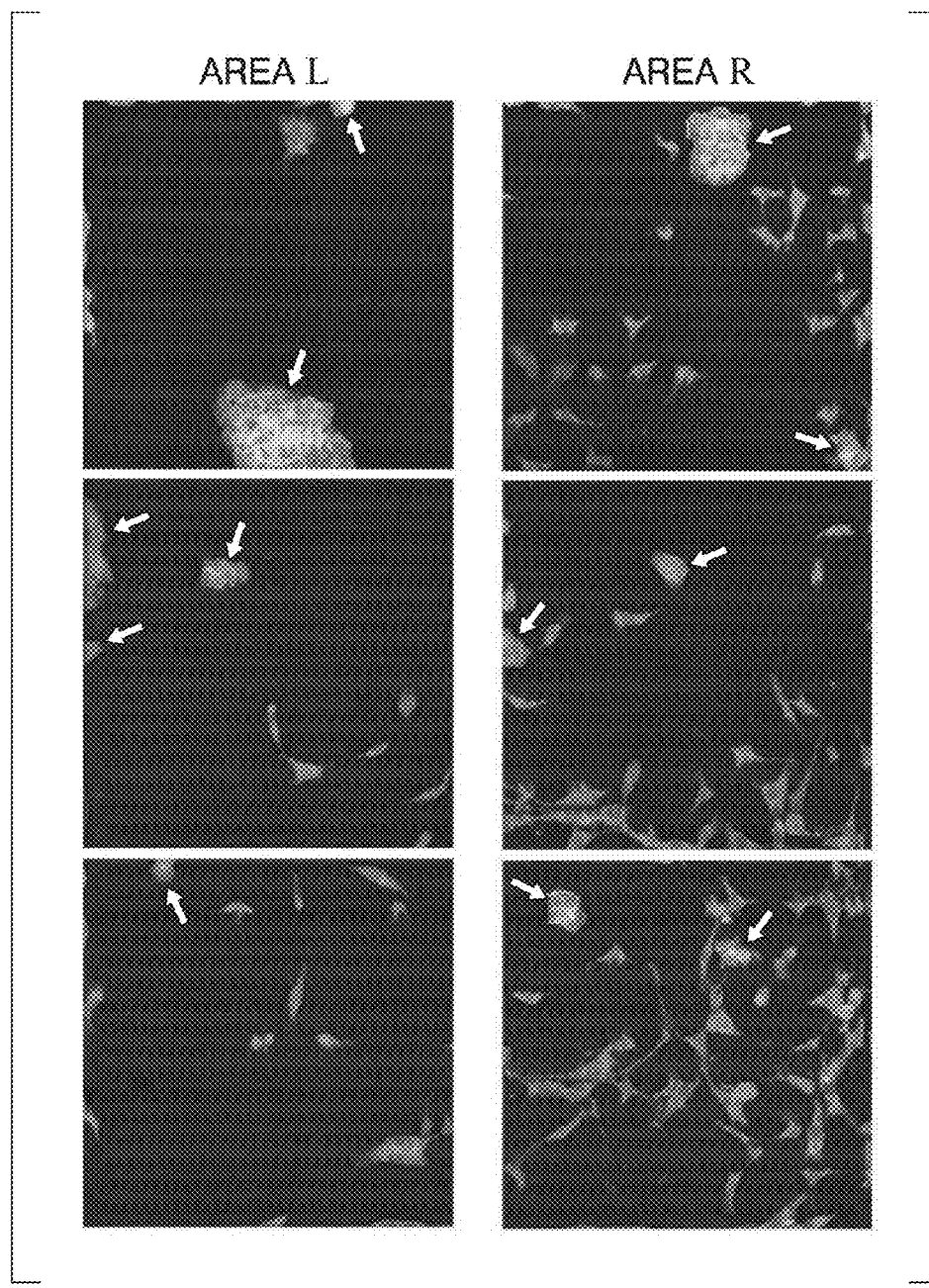
FIG. 14 shows microscope pictures of HaCaT cells and NIH3T3 cells of an area R and an area L of the substrate 4. In the pictures, a green color (with an arrow) indicates the HaCaT cells, and a red color (without an arrow) indicates the NIH3T3 cells.

Similarly to the above (4), migration directionality of HaCaT cells and NIH3T3 cells on the substrate of Example 2(2) was confirmed. Pictures obtained by capturing the substrate 4 are shown in FIG. 14.

Migration of HaCaT cells (green indicated by white arrows) was hardly observed. However, migration of NIH3T3 cells (red without arrows) to the area R was confirmed.

(6) Confirmation 2 of Migration Directionality of Cells of Two Types

Figure 16:
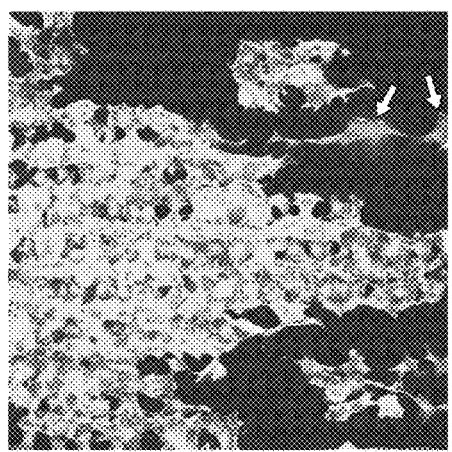
FIG. 16 shows microscope pictures of HaCaT cells and NIH3T3 cells of the area R and the area L of the substrate 4.
Figure 16:
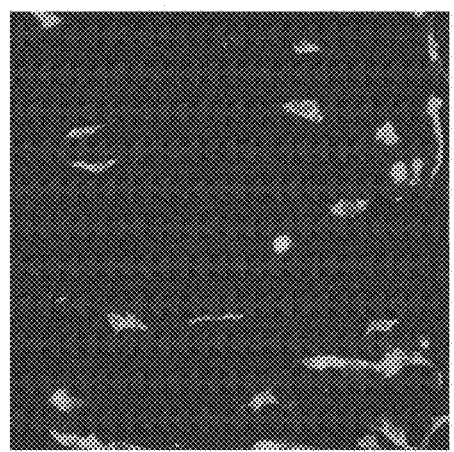

Similarly to the above (4), migration directionality of HaCaT cells and NIH3T3 cells on the substrate of Example 2(2) was confirmed. Pictures obtained by capturing the substrate 4 are shown in FIG. 16.

In the area L on the left in the drawing, a great number of HaCaT cells (green without arrows) were observed. However, only a very small number of NIH3T3 cells (red indicated by white arrows) were present. On the other hand, in the area R on the right in the drawing, all cells in the field of view were NIH3T3 cells (red without arrows).

As a result, it was confirmed that HaCaT cells hardly moved, but a great number of NIH3T3 cells moved to the area R.

INDUSTRIAL APPLICABILITY

According to the present invention, there is provided a technology by which it is possible to identify or separate cells while maintaining original functions of the cells, and it is possible to evaluate an abundance of cells of each type in a cell suspension or a biological tissue, and invasiveness of cancerous cells. In addition, according to the present invention, since there is no need to use a chemical substance, a growth factor, and an antibody in order to move the cells, it is possible to separate cells while maintaining properties of the cells, and provide stable cells desirable for a cytologic diagnosis and a cell therapy.

REFERENCE SIGNS LIST

1 Wall
2 Columnar protrusion
3 Vertex part of columnar protrusion
4 Line perpendicular to two opposing walls
5 One side of columnar protrusion
6 Gradient with respect to perpendicular line of wall
7 Interval between vertex parts of two columnar protrusions
8 Distance between surface connecting vertex parts of columnar protrusions of one wall and surface connecting vertex parts of columnar protrusions of the other wall
9 Width of wall

The invention claimed is:

1. A control substrate which controls a movement direction of animal cells, wherein a surface of the substrate includes a plurality of grooves, the grooves are formed from two opposing walls and a bottom provided between the two opposing walls, and the two opposing walls forming the grooves include continuous columnar protrusions, wherein the columnar protrusions:

i) have a shape wherein each columnar protrusion has at least one vertex part in a horizontal cross section; and
  ii) are provided at positions such that columnar protrusions formed in a wall and columnar protrusions formed in the opposing wall are arranged alternately; and wherein a direction of the protrusions is inclined to one direction with respect to a distance direction in which the distance toward the opposing wall is measured.

2. The substrate according to claim 1, wherein an interval between vertex parts of adjacent columnar protrusions in a single wall is 3 μm to 20 μm.

3. The substrate according to claim 1, wherein the wall has a height of 10 to 40 μm.

4. The substrate according to claim 1, wherein a distance between the opposing walls is 2 μm to 20 μm.

5. The substrate according to claim 1, wherein a direction of the protrusion faces a direction of 10 and 80 degrees with respect to a perpendicular direction toward the opposing wall, so that a migration direction of cells is controlled to be a direction the protrusion faces.

6. The substrate according to claim 1, wherein the columnar protrusion has a horizontal cross-sectional shape that is a polygon with six or less sides.

7. The substrate according to claim 1, wherein the substrate is made of a material selected from the group consisting of silicon, glass, a plastic and a metal.

8. A method of identifying cells of two or more different types based on a moving capability, the method comprising: adding a cell suspension including cells of two or more different types to one end of a groove of the substrate according to claim 1; maintaining the substrate under conditions in which the cells are able to survive; and identifying a type of the cells along a groove direction of the groove of the maintained substrate.

9. A method of separating cells of two or more different types based on a moving capability, the method comprising: adding a cell suspension including cells of two or more different types to one end of a groove of the substrate according to claim 1; maintaining the substrate under conditions in which the cells survive; and collecting cells on the maintained substrate.

* * * * *